US012558573B2

(12) United States Patent
Yi et al.

(10) Patent No.: US 12,558,573 B2
(45) Date of Patent: Feb. 24, 2026

(54) ELECTRODE STRUCTURE USING TRANSDUCER HOLDER OF TRANSDUCER ARRAY OF HIGH-INTENSITY FOCUSED ULTRASOUND GENERATION DEVICE, AND TRANSDUCER ARRAY

(71) Applicant: JEISYS MEDICAL INC., Seoul (KR)

(72) Inventors: Won Ju Yi, Seoul (KR); Eun Kyung Gong, Seoul (KR); Soo Min Hwang, Seoul (KR); Dong Hwan Kang, Seoul (KR)

(73) Assignee: JEISYS MEDICAL INC., Seoul (KR)

( * ) Notice: Subject to any disclaimer, the term of this patent is extended or adjusted under 35 U.S.C. 154(b) by 0 days.

(21) Appl. No.: 18/697,507

(22) PCT Filed: Sep. 16, 2022

(86) PCT No.: PCT/KR2022/013876
§ 371 (c)(1),
(2) Date: Apr. 1, 2024

(87) PCT Pub. No.: WO2023/075143
PCT Pub. Date: May 4, 2023

(65) Prior Publication Data
US 2024/0408417 A1 Dec. 12, 2024

(30) Foreign Application Priority Data
Nov. 1, 2021 (KR) ........................ 10-2021-0148184

(51) Int. Cl.
*A61N 7/02* (2006.01)
*A61N 7/00* (2006.01)
(52) U.S. Cl.
CPC ........ *A61N 7/02* (2013.01); *A61N 2007/0026* (2013.01); *A61N 2007/0078* (2013.01)

(58) Field of Classification Search
CPC .............. A61N 7/02; A61N 2007/0078; A61N 2007/0095; A61N 2007/0026;
(Continued)

(56) References Cited

U.S. PATENT DOCUMENTS 3,561,734 A * 2/1971 Antonevich ......... G10K 11/004
366/127
3,973,430 A * 8/1976 Cirulis ................. G01N 29/024
73/61.49
(Continued)

FOREIGN PATENT DOCUMENTS

JP H0871079 A 3/1996
JP 2001104356 A 4/2001
(Continued)

OTHER PUBLICATIONS

International Search Report for PCT/KR2022/013876 mailed Jan. 19, 2023 from Korean Intellectual Property Office.
(Continued)

*Primary Examiner* — Bo Joseph Peng

(57) ABSTRACT

The present invention includes: multiple transducers individually mounted to an ultrasonic radiation frame by transducer holders; and an electrode in which at least a part of each of the transducer holders is formed of a conductive material, wherein the front surfaces of the transducers are in contact with and thus electrically connected to the transducer holders, and the rear surfaces of the transducers are electrically connected through an electrode wire, so that there is no need to solder an electrode wire to the front surfaces of the transducers, thereby preventing a leakage due to a solder structure and facilitating the manufacturing thereof.

20 Claims, 7 Drawing Sheets

(58) Field of Classification Search
CPC .... A61N 2007/0056; A61N 2007/0065; A61N
2007/025; B06B 1/06; B06B 1/0607;
B06B 2201/40; B06B 2201/76; A61B
8/00; G10K 11/004; G10K 9/22
See application file for complete search history.

(56) References Cited

U.S. PATENT DOCUMENTS

| | | | | |
|---|---|---|---|---|
| 5,313,839 | A * | 5/1994 | Ridenour | G01L 19/142 |
| | | | | 73/756 |
| 6,094,402 | A * | 7/2000 | Cooper | G10K 9/22 |
| | | | | 367/173 |
| 6,216,025 | B1 * | 4/2001 | Kruger | A61B 8/0825 |
| | | | | 600/407 |
| 6,487,447 | B1 * | 11/2002 | Weimann | A61M 37/0092 |
| | | | | 604/20 |
| 7,525,097 | B2 * | 4/2009 | Dorscheid | A61B 6/4291 |
| | | | | 250/370.11 |
| 10,502,713 | B2 * | 12/2019 | Kandori | G01N 29/2418 |
| 2006/0103265 | A1 * | 5/2006 | Miyoshi | B06B 1/0633 |
| | | | | 310/326 |
| 2007/0253582 | A1 * | 11/2007 | Trochesset | G10K 9/122 |
| | | | | 381/190 |
| 2010/0312118 | A1 * | 12/2010 | Horzewski | A61B 6/037 |
| | | | | 600/458 |
| 2011/0011111 | A1 * | 1/2011 | Martin | G10K 11/004 |
| | | | | 165/104.33 |
| 2013/0289593 | A1 | 10/2013 | Hall et al. | |
| 2014/0188011 | A1 * | 7/2014 | Wurster | A61N 7/00 |
| | | | | 601/2 |
| 2015/0042206 | A1 * | 2/2015 | Nguyen | G01F 1/662 |
| | | | | 310/311 |
| 2015/0243273 | A1 * | 8/2015 | Wu | G10K 11/004 |
| | | | | 428/35.8 |
| 2017/0059530 | A1 * | 3/2017 | Kandori | A61B 5/0095 |
| 2018/0275305 | A1 * | 9/2018 | Matsumoto | G01V 1/523 |
| 2021/0051416 | A1 * | 2/2021 | Masters | H04R 17/10 |
| 2025/0018228 | A1 * | 1/2025 | Yi | A61N 7/02 |

FOREIGN PATENT DOCUMENTS

| | | | |
|---|---|---|---|
| JP | 2015516233 | A | 6/2015 |
| JP | 2017042204 | A | 3/2017 |
| KR | 10-2011-0074326 | A | 6/2011 |
| KR | 10-2013-0055972 | A | 5/2013 |
| KR | 10-1457666 | B1 | 11/2014 |
| KR | 10-1554846 | B1 | 9/2015 |
| KR | 20170028862 | A | 3/2017 |
| KR | 10-1952588 | B1 | 2/2019 |
| KR | 10-2021-0003460 | A | 1/2021 |

OTHER PUBLICATIONS

Japanese Patent Office, Notice of Reasons for Refusal regarding Application No. 2024-520025, Jan. 29, 2025.
Korean Patent Office, Notice of Submission of Opinions regarding Application No. 10-2023-0151363, Nov. 4, 2024.
International Preliminary Report on Patentability received for PCT Patent Application No. PCT/KR2022/013876, mailed on May 16, 2024, 11 pages (6 pages of English Translation and 5 pages of Original Document).

* cited by examiner

ELECTRODE STRUCTURE USING TRANSDUCER HOLDER OF TRANSDUCER ARRAY OF HIGH-INTENSITY FOCUSED ULTRASOUND GENERATION DEVICE, AND TRANSDUCER ARRAY

CROSS REFERENCE TO PRIOR APPLICATIONS

This application is the 35 U.S.C. 371 national stage of international application PCT/KR2022/013876 filed on Sep. 16, 2022 which claims priority to Korean Patent Application No. 10-2021-0148184 filed on Nov. 1, 2021. The entire contents of each of the above-identified applications are hereby incorporated by reference.

TECHNICAL FIELD

The present invention relates to an electrode structure using a transducer holder of a transducer array of a high-intensity focused ultrasound generation device, and a transducer array, and more particularly, to an electrode structure using a transducer holder of a transducer array of a high-intensity focused ultrasound generation device, and a transducer array, whereby multiple transducers individually mounted to an ultrasonic radiation frame by transducer holders and at least a part of each of the transducer holders is formed of a conductive material so that an electrode structure is simplified and thus damage of the transducers can be prevented.

BACKGROUND ART

In general, high-intensity focused ultrasound generators are apparatuses that generate high-intensity ultrasonic energy by focusing ultrasonic waves generated by transducers and rise the temperature of an affected area by irradiating high-intensity ultrasonic energy to the affected area of a patient so that the affected area can be treated without surgery.

When several tens or several hundreds of transducers are used in a high-intensity focused ultrasound generator according to the related art, a plurality of transducers are mounted on the front surface of an ultrasonic radiation frame and then the whole front surface of the ultrasonic radiation frame is coated with glue to form a waterproof layer so that the plurality of transducers are fixed by the waterproof layer and a leakage can be prevented.

However, since ultrasonic energy generated by the transducers in a forward direction is absorbed by the waterproof layer, there is a problem that input voltages need to be increased to compensate therefor, and there is a problem that the ultrasonic radiation frame needs to be replaced even if only one of the plurality of transducers breaks down.

DETAILED DESCRIPTION OF THE INVENTION

Technical Problem

The present invention provides an electrode structure using a transducer holder of a transducer array of a high-intensity focused ultrasound generation device, and a transducer array, whereby a leakage can be blocked and replacement and repair can be easily performed.

Technical Solution

According to an aspect of the present invention, there is provided an electrode structure using a transducer holder of a transducer array of a a high-intensity focused ultrasound generation device, the electrode structure including: an ultrasonic radiation frame having a concave front surface and a plurality of coupling holes formed therein; a plurality of transducer holders respectively inserted into the plurality of coupling holes in front of the ultrasonic radiation frame and detachably coupled to the ultrasonic radiation frame while passing through the ultrasonic radiation frame; and a plurality of transducers respectively mounted in the plurality of transducer holders so that front surfaces of the plurality of transducers are exposed, wherein a surface of each of the transducer holders may be an electrode formed by being coated with a conductive material, and at least one the front surface and the side surface of each of the transducers may be in contact with the electrode and may be electrically connected to the electrode, and the rear surface of the transducer may be coupled to a current supply unit inserted through current supply holes formed in rear of the transducer holder so that current is supplied to the transducer due to a potential difference applied between the electrode and the current supply unit.

Each of the transducer holders may include: a head portion mounted on the front surface of the ultrasonic radiation frame and having a seating groove in which the transducer is insertedly seated, formed therein; and a body portion extending from the head portion backward and coupled to the coupling holes using a fastening member from a rear of the ultrasonic radiation frame while passing through the coupling holes.

The current supply holes may be formed in the body portion of the transducer holder so that the current supply unit passes through the current supply holes and can be pulled out to the rear of the ultrasonic radiation frame, and sealing between the current supply unit and the current supply holes may be performed using glue for waterproofing.

In the head portion of the transducer holder, at least a part of side surfaces of the seating groove may be formed to be open.

At least one support protrusion may be formed on the head portion of the transducer holder to protrude from a bottom surface of the seating groove, to support a lower surface of the transducer and to form a separation space between the transducer and the bottom surface.

The support protrusion may be formed of a non-conductive material.

A locking protrusion may be formed on the head portion of the transducer holder to protrude from the bottom surface of the seating groove and to have a tip bent inwardly so as to prevent deviation of the transducer inserted into the seating groove.

The body portion of the transducer holder may include: a shaft portion extending from the head portion backward and being pressed into the coupling holes; and a screw portion extending from the shaft portion backward and coupled to the fastening member in the rear of the ultrasonic radiation frame after passing through the coupling holes, and sealing between the transducer holder and the ultrasonic radiation frame may be performed using a sealing member, and the sealing member may include an O-ring inserted outside the shaft portion, and an O-ring pressing member inserted outside the shaft portion from a rear of the O-ring and allowing the O-ring to be in close contact with the rear surface of the ultrasonic radiation frame.

Adhesion between at least one of the rear surface and the side surface of each of the transducers may be performed using an adhering member, and sealing between an inside of the transducer holder and the transducer may be performed so that vibration of the transducer is enabled inside the transducer holder, and sealing between the transducer holder and the ultrasonic radiation frame may be performed using a sealing member, and the adhering member may include a flexible glue, and the sealing member may include an O-ring inserted into a ring-shaped groove formed from the head portion in the rear surface toward the ultrasonic radiation frame.

The current supply unit may include an electrode wire inserted through electrode wire holes formed in the body portion.

The side surface and the rear surface of the transducer may be coated with at least one of a waterproofing material and a non-conductive material.

According to another aspect of the present invention, there is provided an electrode structure using a transducer holder of a transducer array of a high-intensity focused ultrasound generation device, the electrode structure including: an ultrasonic radiation frame having a concave front surface and a plurality of coupling holes formed therein; a plurality of transducer holders respectively inserted into the plurality of coupling holes in front of the ultrasonic radiation frame and detachably coupled to the ultrasonic radiation frame while passing through the ultrasonic radiation frame; and a plurality of transducers respectively mounted in the plurality of transducer holders so that front surfaces of the plurality of transducers are exposed, wherein each of the transducer holders may be an electrode formed of a conductive material, and at least one of the front surface and the side surface of each of the transducers may be in contact with the electrode and is electrically connected to the electrode, and the rear surface of the transducer may be coupled to a current supply unit inserted through current supply holes formed in rear of the transducer holder so that current is supplied to the transducer due to a potential difference applied between the electrode and the current supply unit.

Each of the transducer holders may include: a head portion mounted on the front surface of the ultrasonic radiation frame and having a seating groove in which the transducer is insertedly seated, formed therein; and a body portion extending from the head portion backward and coupled to the coupling holes using a fastening member from a rear of the ultrasonic radiation frame while passing through the coupling holes.

The current supply holes may be formed in the body portion of the transducer holder so that the current supply unit passes through the current supply holes and can be pulled out to the rear of the ultrasonic radiation frame, and sealing between the current supply unit and the current supply holes may be performed using glue for waterproofing.

At least one support protrusion may be formed on the head portion of the transducer holder to protrude from a bottom surface of the seating groove, to support a lower surface of the transducer and to form a separation space between the transducer and the bottom surface.

At least a part of the side surface of the seating groove may be formed to be open, and the support protrusion may be formed of a non-conductive material.

A locking protrusion may be formed on the head portion of the transducer holder to protrude from the bottom surface of the seating groove and to have a tip bent inwardly so as to prevent deviation of the transducer inserted into the seating groove.

The current supply unit may include an electrode wire inserted through electrode wire holes formed in the body portion.

The side surface and the rear surface of the transducer may be coated with at least one of a waterproofing material and a non-conductive material.

According to another aspect of the present invention, there is provided a transducer array of a high-intensity focused ultrasound generation device to which the electrode structure is applied.

Effects of the Invention

The present invention includes a plurality of transducers individually mounted on an ultrasonic radiation frame using transducer holders, and an electrode in which at least a part of each of the transducer holders is formed of a conductive material, and the front surfaces of the transducers are in contact with and thus electrically connected to the transducer holders, and the rear surfaces of the transducers are electrically connected through an electrode wire, so that there is no need to solder an electrode wire to the front surfaces of the transducers, thereby preventing a leakage due to a solder structure and facilitating the manufacturing thereof.

In addition, the transducers are configured to be seated on support protrusions of the transducer holders, so as to prevent the electrode wire coupled to the lower surfaces of the transducers from coming into contact with the transducer holders, thereby preventing a short-circuiting phenomenon, and stabilize the electrode structure and thus enhance a vibration wave effect.

MODE OF THE INVENTION

Hereinafter, embodiments of the present invention will be described in detail with reference to the accompanying drawings.

A high-intensity focused ultrasound generation device according to an embodiment of the present invention is a device using high-intensity focused ultrasound (HIFU). The high-intensity focused ultrasound generation device may include a transducer array in which several tens or several hundreds of transducers are radially arranged, thereby treating the affected area of a patient with tumor, etc., stimulating the brain to treat diseases such as Alzheimer's or depression, and increasing immunity by heating specific areas.

Figure 1:
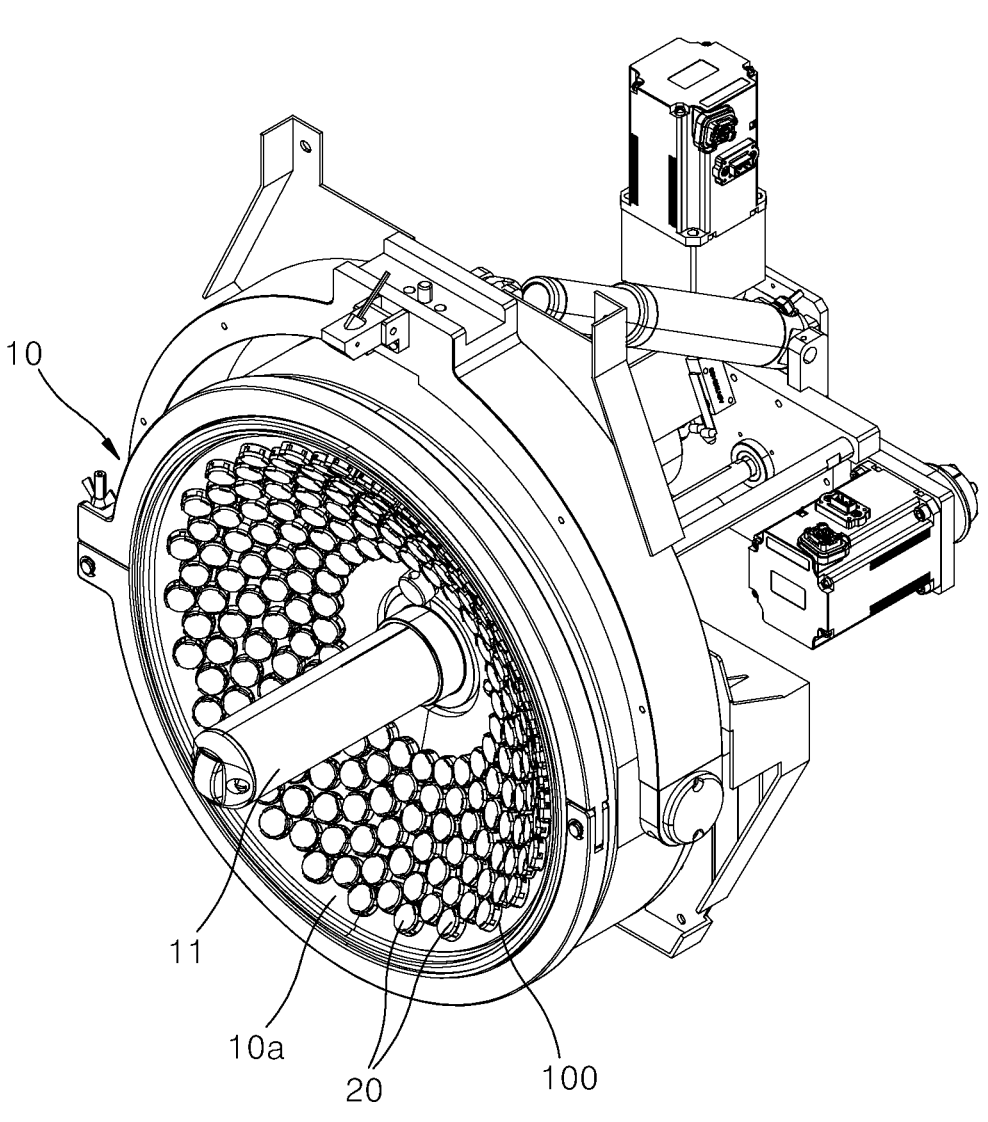
FIG. 1 is a perspective view illustrating a head module of a high-intensity focused ultrasound generation device according to an embodiment of the present invention.
Figure 2:
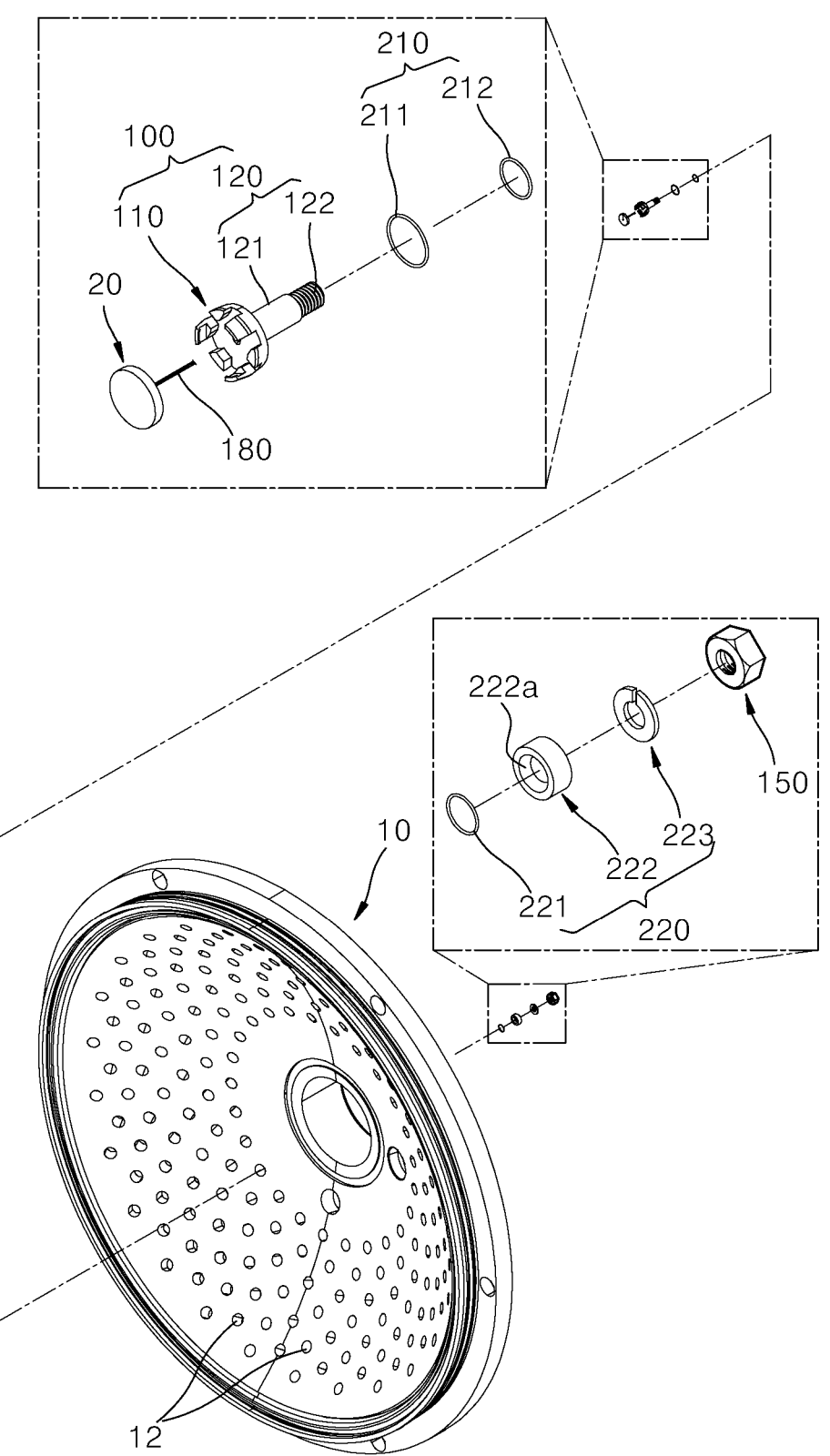
FIG. 2 is an exploded perspective view illustrating a coupling structure of an ultrasonic radiation frame and a transducer holder according to an embodiment of the present invention.

FIG. 1 is a perspective view illustrating a head module of a high-intensity focused ultrasound generation device according to an embodiment of the present invention. FIG. 2 is an exploded perspective view illustrating a coupling structure of an ultrasonic radiation frame and a transducer holder according to an embodiment of the present invention.

Referring to FIGS. 1 and 2, the head module of the high-intensity focused ultrasound generation device includes an ultrasonic radiation frame 10, a plurality of transducers 20, and a plurality of transducer holders 100.

The ultrasonic radiation frame 10 includes a probe 11 coupled to the center of a front surface 10a, and a plurality of coupling holes 12 arranged radially based on the probe 11. The ultrasonic radiation frame 10 is formed to have a dish shape with a concave front surface to focus ultrasonic waves radiating from the plurality of transducers 20 to radiate the ultrasonic waves to one place.

The plurality of coupling holes 12 are through holes spaced apart from each other at certain intervals. The number of the coupling holes 12 is set according to the number of the transducers 20.

The plurality of transducers 20 may include a piezoelectric element. Each of the transducers 20 generates ultrasonic waves when receiving voltages 20. An example in which the transducer 20 has a disc shape, will be described. Several tens or several hundreds of transducers 20 are radially arranged to form a transducer array. The number of the transducers 20 may be set according to ultrasonic energy to radiate.

The transducer holder 100 is detachably coupled to each of the plurality of coupling holes 12. Each transducer 20 is coupled to the transducer holder 100.

Figure 3:
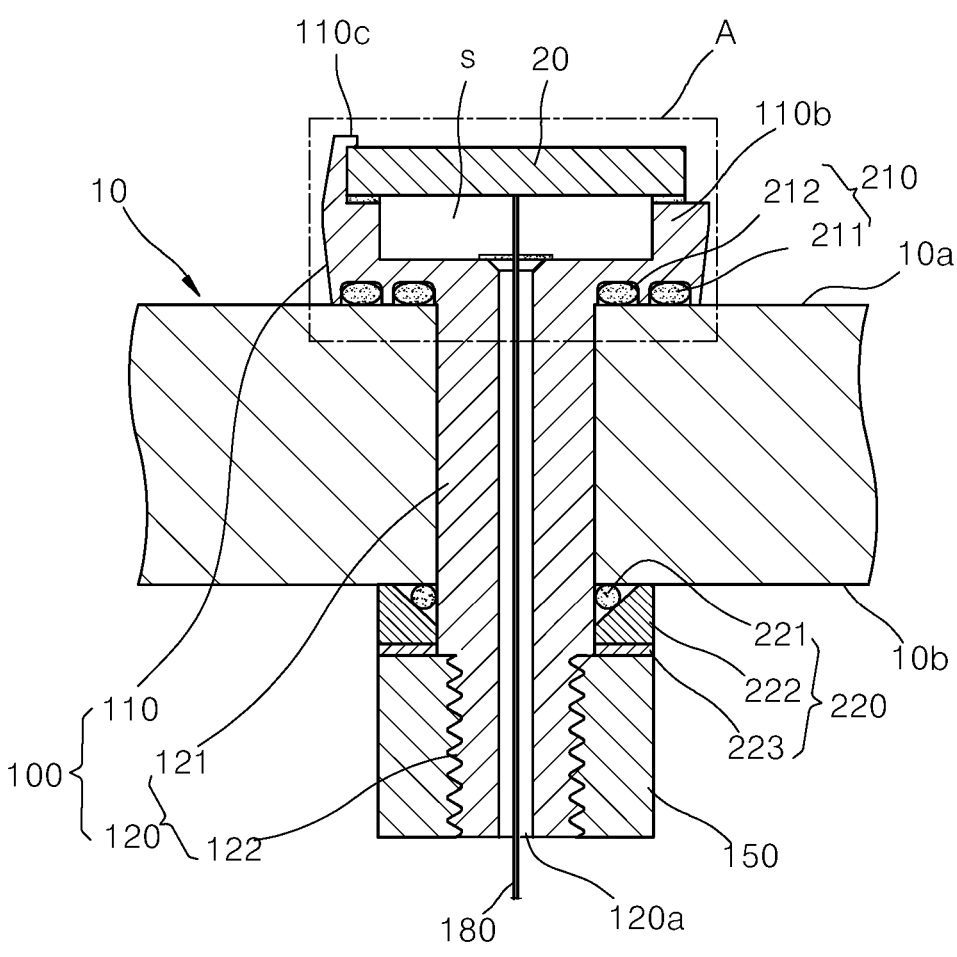
FIG. 3 is a cross-sectional view illustrating the coupling structure of the ultrasonic radiation frame and the transducer holder according to an embodiment of the present invention.
Figure 4:
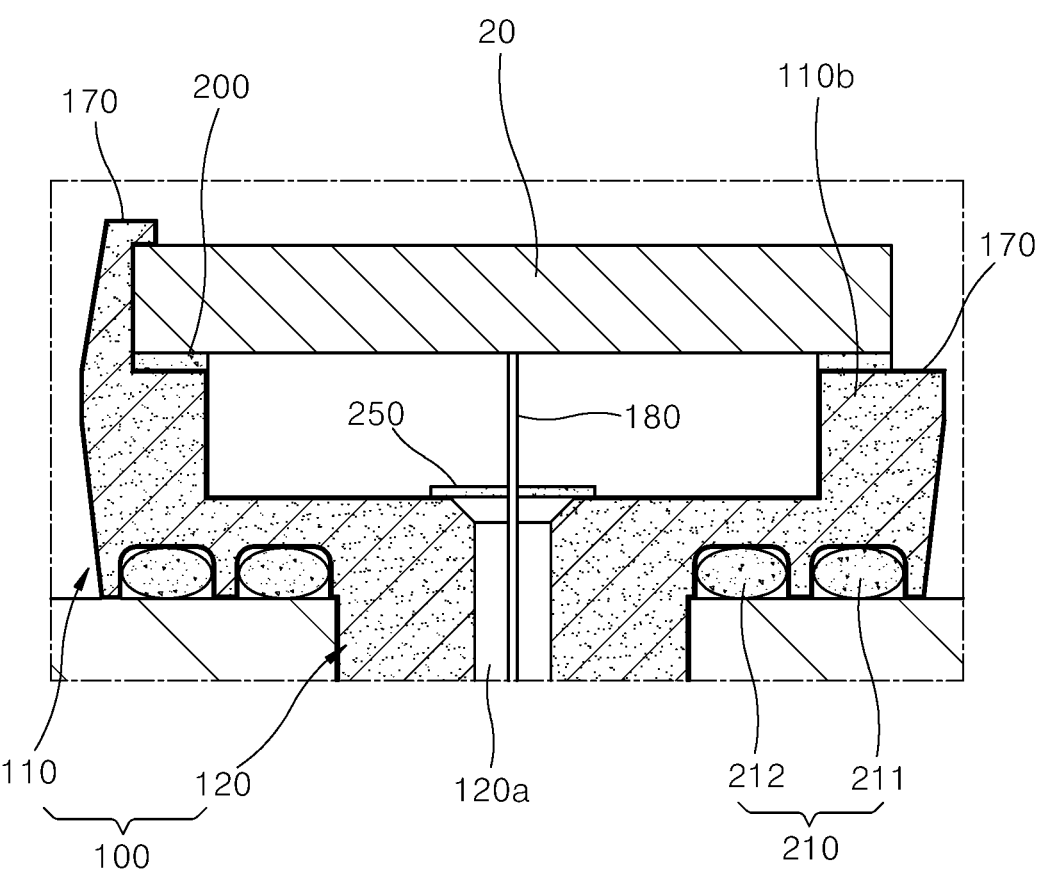
FIG. 4 is an enlarge view of a portion A of FIG. 3.
Figure 5:
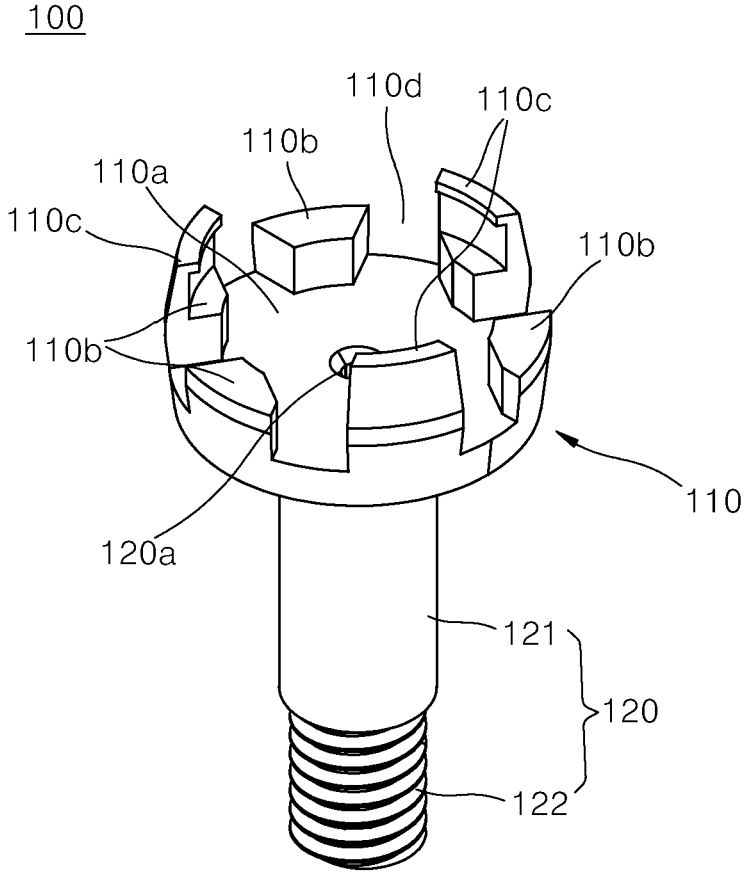
FIG. 5 is a front perspective view of a transducer holder according to an embodiment of the present invention.
Figure 6:
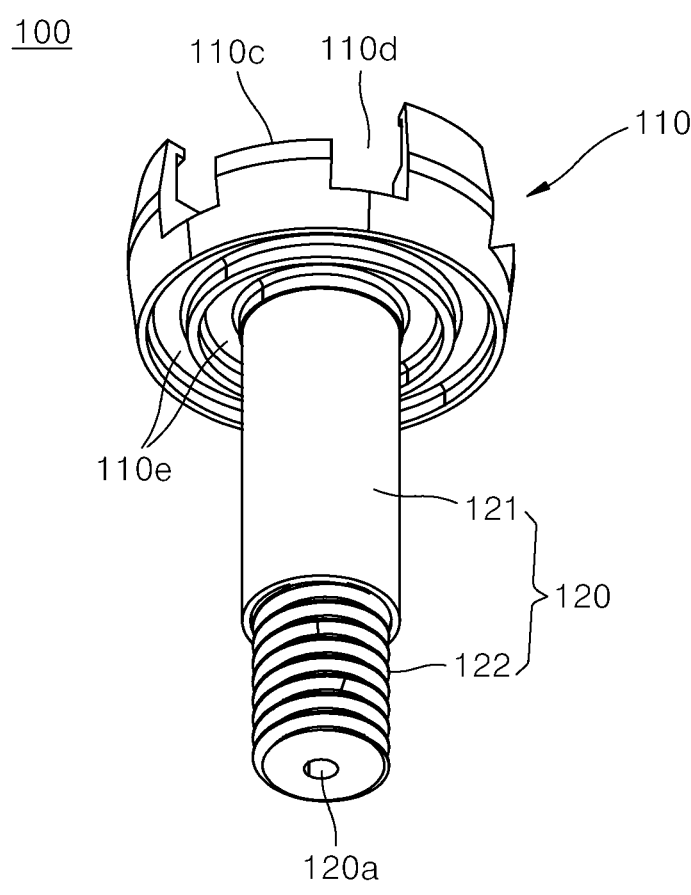
FIG. 6 is a rear perspective view of the transducer holder shown in FIG. 5.

Referring to FIGS. 3 through 5, the transducer holder 100 includes a head portion 110 with a seating groove 110a into which the transducer 20 is insertedly seated, and a body portion 120 which extends from the head portion 110 backward and is coupled to the coupling holes 12.

The head portion 110 is greater in diameter than the coupling holes 12 so as to be seated on the front surface 10a of the ultrasonic radiation frame 10. The head portion 110 includes the seating groove 110a, a support protrusion 110b, a locking protrusion 110c, and an opening 110d.

The seating groove 110a is formed in the front of the head portion 110 to have an open front surface, such that the transducer 20 is seated thereon.

The support protrusion 110b is a stepped protrusion that protrudes from a bottom surface of the seating groove 110a in a forward direction to a certain height so as to support a lower surface of the transducer 20. The support protrusion 110b forms a separation space S between the lower surface of the transducer 20 and the bottom surface of the seating groove 110a to form a passage through which an electrode wire 180 coupled to the transducer 20 passes, thereby implementing an electrode structure stably and maximizing vibration wave energy of the transducer 20 by enabling vibration of the transducer 20. An example, in which the support protrusion 110b is formed in plurality and a plurality of support protrusions 110b are spaced apart from each other at certain intervals, will be described. However, embodiments are not limited thereto, and one support protrusion 110b may also be in the center of the bottom surface of the seating groove 110a. Also, the support protrusions 110b may also be formed integrally with the head portion 110, and of courses, the support protrusions 110b may also be formed by coating a non-conductive material, i.e., glue, onto the bottom surface of the seating groove 110a.

The locking protrusion 110c protrudes from the bottom surface of the seating groove 110a and has a tip bent inwardly so that deviation of the transducer 20 inserted into the seating groove 110a can be prevented. The tip of the locking protrusion 110c may be changed as long as it has a shape in which deviation of the transducer 20 can be prevented, such as a hook shape, etc. The locking protrusion 110c is formed in plurality, and the plurality of locking protrusions 110c are spaced apart from each other at certain intervals. In the present embodiment, an example, in which some of the plurality of locking protrusions 110c protrude from the support protrusions 110b, will be described.

The opening 110d is cut from side surfaces of the seating groove 110a and is formed to be open. There is an advantage that assembly is easy due to the opening 110d. Also, the opening 110d allows the transducer 20 to vibrate inside the seating groove 110a so that vibration wave energy of the transducer 20 may be maximized.

It is preferable that the body portion 120 is formed to extend from the head portion 110 backward and to pass through the coupling holes 12. The body portion 120 is formed to have a smaller diameter than a diameter of the head portion 110. Current supply holes are formed in the center of the body portion 120 so that a current supply unit to be described below may pass through the current supply holes.

The body portion 120 includes a shaft portion 121 and a screw portion 122.

The shaft portion 121 extends from the head portion 110 backward and is formed in a cylindrical shape to be pressed into the coupling holes 12.

The screw portion 122 extends from the shaft portion 121 backward, and has a screw thread to be fastened to an outer circumferential surface of the screw portion 122 by a fastening member 150.

The fastening member 50 is preferably, a nut, but embodiments are not limited thereto.

Meanwhile, FIG. 3 is a cross-sectional view 3 illustrating the coupling structure of the ultrasonic radiation frame and the transducer holder according to an embodiment of the present invention.

An example in which the adhering member is a flexible glue, will be described. A flexible glue layer 200 is formed between at least one of the rear surface and the side surface of the transducer 20 and the head portion 110 using the flexible glue. The flexible glue may be a silicon or epoxy-based glue, and may be applied as long as it is formed of a flexible material.

In the present embodiment, an example, in which the flexible glue layer 200 is formed between the rear surface of the transducer 20 and the support protrusion 110b, will be described. However, embodiments are not limited thereto, and the flexible glue layer 200 may be formed between the side surface of the transducer 20 and an inner side of each of the locking protrusions 110c. That is, the flexible glue layer 200 may be applied in any location where the front surface of the transducer 20 is not blocked.

The transducer 20 is adhered to the transducer holder 100 and is fixed thereto using the flexible glue, so that the location of the transducer 20 is fixed inside the transducer holder 100 and the transducer 20 may vibrate and thus, the vibration wave energy loss of the transducer 20 may be minimized. Also, since the glue is not applied onto the front surface of the transducer 20, the loss of ultrasonic energy radiating from the transducer 20 forward can be prevented. That is, since the flexible glue layer 200 is formed at only the rear surface or side surface of the transducer 20, the flexible glue layer 200 does not cover the front surface of the transducer 20 and thus, there are no restrictions in radiation of ultrasonic energy through the front surface.

Also, sealing between the transducer holder 100 and the ultrasonic radiation frame 10 is performed using a sealing member.

The sealing member includes a first sealing member 210 for sealing between the head portion 110 of the transducer holder 100 and the front surface 10*a* of the ultrasonic radiation frame 10, and a second sealing member 220 for sealing between the body portion 120 and a rear surface 10*b* of the ultrasonic radiation frame 10.

An example, in which the first sealing member 210 includes two first and second O-rings 211 and 212 that are inserted into the rear surface of the head portion 110 and coupled to each other, will be described. However, embodiments are not limited thereto, and the number of the first sealing members 210 may be changed in various ways and applied. Also, the first sealing member 210 may be used as long as it is formed of various materials such as silicon, rubber or the like and has a sealing structure, except for an O-ring.

It is preferable that the first O-ring 211 and the second O-ring 212 are formed to have different diameters. The first O-ring 211 and the second O-ring 212 are inserted into a ring-shaped groove 110*e* formed in the rear surface of the head portion 110 and are sealed while being in close contact with the front surface 10*a* of the ultrasonic radiation frame 10.

The second sealing member 220 includes a third O-ring 221 inserted outside the shaft portion 121 of the body portion 120, and an O-ring pressing member 222 inserted outside the shaft portion 121 in a backward direction of the third O-ring 221 and allowing the third O-ring 221 to be in close contact with the rear surface 10*b* of the ultrasonic radiation frame 10.

The O-ring pressing member 222 is formed to have a ring shape, and includes an inclined surface 222*a* on which a part of the third O-ring 221 is seated and which is formed on the front surface of the O-ring pressing member 222.

The second sealing member 220 may further include a washer 223 provided between the O-ring pressing member 222 and the fastening member 150. The washer 223 is not an essential component of the second sealing member 220 and may be additionally provided. The washer 223 may seal the third O-ring 221 and the O-ring pressing member 222 and may hold the transducer holder 100.

The second sealing member 220 may be used as long as it is formed of various materials such as silicon, rubber, etc. and seals, except for an O-ring or a washer.

Also, a glue layer for waterproofing 250 is formed between the electrical wire holes 120*a* of the transducer holder 100 and an electrode wire 180 to be described later using glue for waterproofing. The glue for waterproofing that is the same as the flexible glue may be used. Also, of course, the glue layer for waterproofing 250 may also be formed to fill the separation space S fully using the glue for waterproofing.

Meanwhile, an electrode structure using the transducer holder 100 will be described with reference to FIG. 4 as below.

The surface of the transducer holder 100 is coated with a conductive material to form an electrode 170, and the inside of the transducer holder 100 is formed of a non-conductive material.

The electrode 170 is a coating layer formed by coating the entire surface of the transducer folder 100 with the conductive material, and is grounded. However, embodiments are not limited thereto, and of course, the electrode 170 may also be formed by coating only a part including a portion contacting the transducer 20 of the surface of the transducer folder 100 with the conductive material. Also, the entire surface of the transducer holder 100 may also be coated with the conductive material, and only the inside of the head portion 110 or the surface excluding the support protrusions 110*b* may be coated with the conductive material. When the entire surface of the transducer holder 100 is coated with the conductive material, at least a part of the side surface and the rear surface of the transducer 20 may be coated with a non-conductive material, thereby preventing a short-circuiting phenomenon. Also, when at least a part of the side surface and the rear surface of the transducer 20 is coated with a waterproofing material, corrosion due to water intrusion and fluctuations in output values can be prevented.

The conductive material may be any material that can be used as an electrode including metal such as silver. An example in which the non-conductive material is a plastic material, will be described.

Thus, the front surface and the side surface of the transducer 20 may be grounded in contact with the electrode 170, and the current supply unit is connected to the rear surface of the transducer 20.

An example, in which the current supply unit is the electrode wire 180, will be described. However, embodiments are not limited thereto, and any portion that is capable of supplying current, such as a pin, a connector, etc., may be used.

The electrode wire 180 is an electrical wire that is coupled to the center of the rear surface of the transducer 20 by soldering and supplies current to the transducer 20.

The electrode wire 180 is disposed to pass through the current supply holes of the transducer holder 100. An example in which the current supply holes are the electrode wire holes 120*a* formed through which the electrode wire 180 passes, will be described.

The electrode wire 180 is pulled out to the rear of the ultrasonic radiation frame 10 through the electrode wire holes 120*a* and is connected to a separate circuit board.

Here, the electrode 170 is set as one of a positive electrode and a negative electrode, and the electrode wire 180 is set as the other one of the positive electrode and the negative electrode, so that current flows through the transducer 20 due to a potential difference applied between the electrode 170 and the electrode wire 180. For example, the electrode 170 may also be set as the positive electrode, and the electrode wire 170 may also be set as a ground electrode, and the electrode 170 may also be set as the ground electrode, and the electrode wire 180 may also be set as the positive electrode.

The transducer 20 is seated on the support protrusions 110*b* so that the separation space S is formed between transducer 20 and the bottom surface of the seating groove 110*a* of the transducer holder 100 and thus the electrode wire 180 is prevented from being in contact with the electrode 170 that is the surface of the transducer holder 100 and thus a short-circuiting phenomenon does not occur.

Thus, there is no need to solder an electrode wire to the front surface of the transducer 20, thereby preventing a leakage due to a solder structure on the front surface of the transducer 20. That is, a leakage can be prevented from occurring inwardly from the front surface of the transducer 20 that is exposed to the front surface of the ultrasonic radiation frame 10 and is in contact with a liquid.

In addition, since there is no need to solder an electrode wire to the front surface of the transducer 20, the electrode structure can be simplified, and damage of the transducer 20 can be prevented.

In addition, in the high-intensity focused ultrasound generation device having the above-described configuration, the plurality of transducers 20 are mounted on the ultrasonic radiation frame 10 using the transducer holder 100, so that sealing between the transducer 20 and the transducer holder 100 is performed using the flexible glue and thus, even if the glue is not applied onto the whole front surface of the ultrasonic radiation frame 10, a leakage can be prevented from occurring inwardly from the front surface of the ultrasonic radiation frame 10.

Also, since the glue is not applied onto the whole front surface of the ultrasonic radiation frame 10, the whole front surface of the transducers 20 is exposed so that the loss of ultrasonic energy radiating from the transducers 20 forward can be prevented. When, as in the related art, the front surfaces of the transducers 20 are blocked by the glue layer, there is a problem that ultrasonic energy is absorbed by the glue layer, but in the present invention, the whole front surface of the transducers 20 is exposed and thus this problem can be prevented.

Also, adhesion between the inside of the transducer holder 100 and the transducer 20 is performed using the flexible glue so that the location of the transducer 20 is fixed and vibration of the transducer 20 is enabled while a gap is prevented and thus, the loss of vibration wave energy of the transducer 20 can be reduced.

Also, the plurality of transducers 20 are individually mounted through the transducer holders 100, and the transducer holders 100 are detachably coupled to the ultrasonic radiation frame 10 and thus, repair and replacement of the transducers 20 may be individually performed.

Also, since the plurality of transducers 20 are individually mounted through the transducer holder 100, the capacity of at least a part of the plurality of transducers 20 may be differently configured. For example, the capacity of transducers arranged at the center of the ultrasonic radiation frame 10 may also be increased, and of course, voltages applied to the plurality of transducers 20 may also be differently controlled.

Also, sealing between the transducer holder 100 and the ultrasonic radiation frame 10 may be performed using a sealing member such as an O-ring, so that a leakage can be prevented from occurring from the front surface of the ultrasonic radiation frame 10 backward and the transducer holders may be easily attached to/detached from the ultrasonic radiation frame.

Meanwhile, in the above-described embodiment, an example in which all of the transducers 20 are coupled to the coupling holes 12 of the ultrasonic radiation frame 10, has been described, but embodiments are not limited thereto, and the transducer 20 may also be provided in only at least a part of the coupling holes 12 according to the capacity of the high-intensity focused ultrasound generation device. When the transducers 20 are provided in only at least a part of the coupling holes 12, the transducer holders 100 are coupled to all of the coupling holes 12, and a holder cover (not shown) for shielding the open front surface may also be detachably coupled to some of the transducer holders 100 to which the transducers 20 are not coupled. The holder cover (not shown) may be formed of a different material from the transducers 20, may have the same shape as the transducers 20 and may be coupled to the transducers 20 using glue. Thus, the mounting number of the transducers 20 can be adjusted so that the energy capacity of the high-intensity focused ultrasound generation device can be adjusted.

Figure 7:
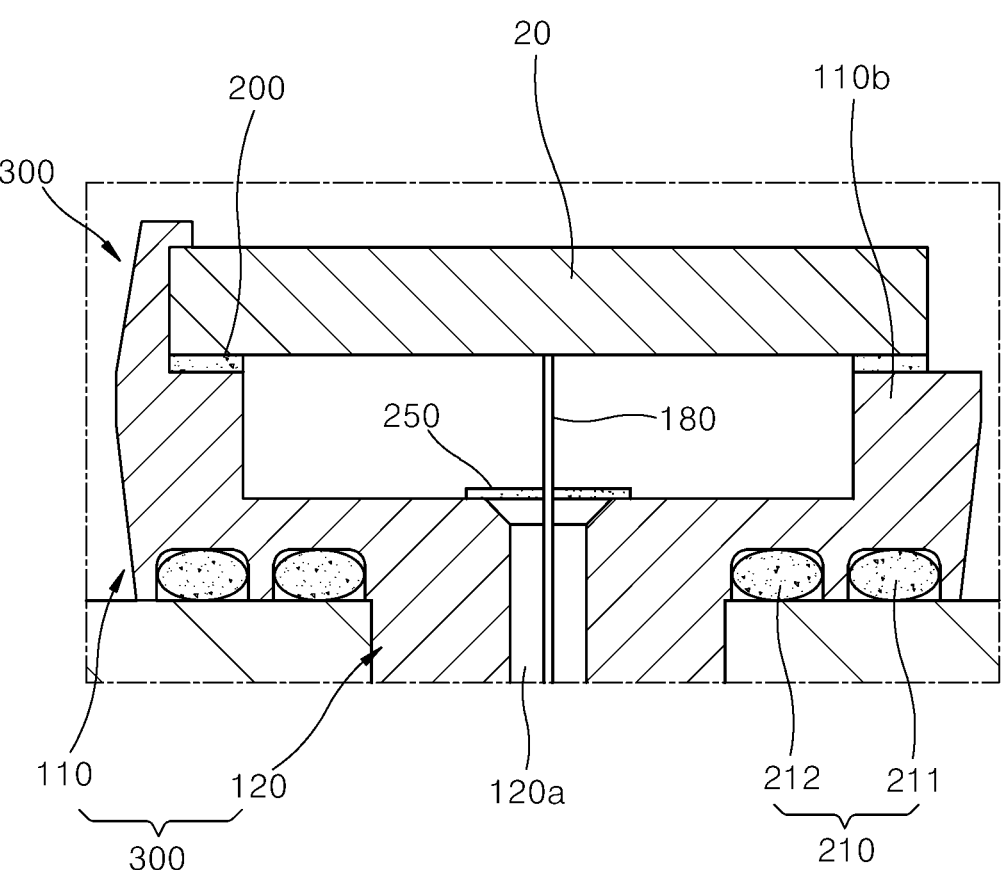
FIG. 7 is a diagram illustrating an electrode structure using transducer holders according to another embodiment of the present invention.

Meanwhile, FIG. 7 is a diagram illustrating an electrode structure using transducer holders according to another embodiment of the present invention.

Referring to FIG. 7, the electrode structure using transducer holders according to another embodiment of the present invention is different from the above-described embodiment in that all of transducer holders 300 include a conductive material, and the other configuration and operation thereof are the same as those of the above-described embodiment and thus, detailed descriptions of a similar configuration are omitted, and differences therebetween will be described.

The transducer holders 300 are formed of the conductive material and are electrodes themselves, and the structure or shape of the transducer holders 300 that is the same as that of the above-described embodiment, is applied.

The conductive material may be any material that may be used as an electrode including metal such as silver.

The front surface and the side surface of the transducer 20 are in contact with the electrode and are grounded, and the electrode wire 180 is connected to the rear surface of the transducer 20.

The electrode wire 180 is an electrical wire that is coupled to the center of the rear surface of the transducer 20 by soldering and supplies current to the transducer 20. The electrode wire 180 is disposed to pass through the electrode wire holes 120a of the transducer holder 100. The electrode wire 180 is pulled out to the rear of the ultrasonic radiation frame 10 through the electrode wire holes 120a and is connected to a separate circuit board.

Here, the transducer holder 300, i.e., the electrode is set as one of a positive electrode and a negative electrode, and the electrode wire 180 is set as the other one of the positive electrode and the negative electrode, so that current flows through the transducer 20 due to a potential difference applied between the electrode and the electrode wire 180. Also, the electrode may also be set as a ground electrode, and the electrode wire 180 may also be set as a positive electrode.

The transducer 20 is seated on the support protrusions 110b so that the separation space S is formed between the transducer 20 and the bottom surface of the seating groove 110a of the transducer holder 100 and thus the electrode wire 180 is prevented from being in contact with the surface of the transducer holder 300, thereby preventing a short-circuiting phenomenon. Also, the support protrusions 110b may be coated with a non-conductive material or may be formed of a non-conductive material.

Thus, there is no need to solder an electrode wire to the front surface of the transducer 20, thereby preventing a leakage due to a solder structure on the front surface of the transducer 20. That is, a leakage can be prevented from occurring inwardly from the front surface of the transducer 20 that is exposed to the front surface of the ultrasonic radiation frame 10 and is in contact with a liquid.

In addition, since there is no need to solder an electrode wire to the front surface of the transducer 20, the electrode structure can be simplified, and damage of the transducer 20 can be prevented. In addition, at least a part of the side surface and the rear surface of the transducer 20 may be coated with a non-conductive material, thereby preventing a short-circuiting phenomenon. Also, when at least a part of the side surface and the rear surface of the transducer 20 is coated with a waterproofing material, corrosion due to water intrusion and fluctuations in output values can be prevented.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

According to the present invention, an electrode structure using a transducer holder of a transducer array of a high-intensity focused ultrasound generation device that is more stable and has excellent durability and reliability, and a transducer array can be manufactured.

The invention claimed is:

1. An electrode structure using a transducer holder of a transducer array of a high-intensity focused ultrasound generation device, the electrode structure comprising:

an ultrasonic radiation frame having a plurality of coupling holes formed therein;

a plurality of transducer holders respectively inserted into the plurality of coupling holes, coupled to the ultrasonic radiation frame and coated with a conductive material, wherein each of the plurality of transducer holders can be detached from the ultrasonic radiation frame;

a plurality of transducers respectively mounted in the plurality of transducer holders;

wherein at least one of a front surface and a side surface of each of the transducers is in contact with a portion coated with the conductive material in the respective transducer holder, is electrically connected to the portion coated with the conductive material, and is grounded;

a rear surface of each transducer is coupled to an electrode wire inserted through a current supply hole formed in a rear of the respective transducer holder and is electrically connected to a circuit board disposed in a rear of the ultrasonic radiation frame; and current is supplied to each transducer due to a potential difference applied between a portion grounded in the transducer and the electrode wire.

2. The electrode structure of claim 1, wherein each of the transducer holders comprises:

a head portion mounted on the front surface of the ultrasonic radiation frame and having a seating groove in which the respective transducer is insertedly seated, formed therein; and a body portion extending from the head portion backward and coupled to the coupling hole using a fastening member from a rear of the ultrasonic radiation frame while passing through the coupling hole.

3. The electrode structure of claim 2, wherein each current supply hole is formed in the body portion of the respective transducer holder so that the electrode wire passes through the current supply hole and can be pulled out to the rear of the ultrasonic radiation frame; and sealing between the electrode wire and the current supply hole is performed using glue for waterproofing.

4. The electrode structure of claim 2, wherein, in the head portion of each transducer holder, at least a part of side surfaces of the seating groove is formed to be open.

5. The electrode structure of claim 2, wherein at least one support protrusion is formed on head portion of the each transducer holder to protrude from a bottom surface of the seating groove, to support a lower surface of the respective transducer and to form a separation space between the transducer and the bottom surface.

6. The electrode structure of claim 5, wherein each support protrusion is formed of a non-conductive material.

7. The electrode structure of claim 2, wherein a locking protrusion is formed on the head portion of each transducer holder to protrude from the bottom surface of the seating groove and to have a tip bent inwardly so as to prevent deviation of the respective transducer inserted into the seating groove.

8. The electrode structure of claim 2, wherein the body portion of each transducer holder comprises:

a shaft portion extending from the head portion backward and being pressed into the coupling hole; and a screw portion extending from the shaft portion backward and coupled to the fastening member in the rear of the ultrasonic radiation frame after passing through the coupling hole.

9. The electrode structure of claim 8, wherein sealing between each transducer holder and the ultrasonic radiation frame is performed using a sealing member, and the sealing member comprises an O-ring inserted outside the shaft portion; and an O-ring pressing member inserted outside the shaft portion from a rear of the O-ring and allowing the O-ring to be in close contact with the rear surface of the ultrasonic radiation frame.

10. The electrode structure of claim 2, wherein adhesion between at least one of the rear surface and the side surface of each of the transducers is performed using an adhering member, and sealing between an inside of the respective transducer holder and the transducer is performed so that vibration of the transducer is enabled inside the transducer holder; and sealing between the transducer holder and the ultrasonic radiation frame is performed using a sealing member.

11. The electrode structure of claim 10, wherein the each sealing member comprises an O-ring inserted into a ring-shaped groove formed from the head portion in the rear surface toward the ultrasonic radiation frame.

12. An electrode structure using a transducer holder of a transducer array of a high-intensity focused ultrasound generation device, the electrode structure comprising:

an ultrasonic radiation frame having a plurality of coupling holes formed therein;

a plurality of transducer holders respectively inserted into the plurality of coupling holes, coupled to the ultrasonic radiation frame while passing through the ultrasonic radiation frame and formed of a conductive material, wherein each of the plurality of transducer holders can be detached from the ultrasonic radiation frame;

a plurality of transducers respectively mounted in the plurality of transducer holders;

wherein at least one of a front surface and a side surface of each of the transducers is in contact with the respective transducer holder, is electrically connected to the transducer holder and is grounded;

a rear surface of each transducer is coupled to an electrode wire inserted through a current supply hole formed in a rear of the transducer holder and is electrically connected to a circuit board disposed in a rear of the ultrasonic radiation frame; and current is supplied to each transducer due to a potential difference applied between a portion grounded in the transducer and the electrode wire.

US 12,558,573 B2

13

13. The electrode structure of claim 12, wherein each of the transducer holders comprises:

a head portion mounted on the front surface of the ultrasonic radiation frame and having a seating groove in which the respective transducer is insertedly seated, formed therein; and a body portion extending from the head portion backward and coupled to the coupling hole using a fastening member from a rear of the ultrasonic radiation frame while passing through the coupling hole.

14. The electrode structure of claim 13, wherein each current supply hole is formed in the body portion of the respective transducer holder so that the electrode wire passes through the current supply hole and can be pulled out to the rear of the ultrasonic radiation frame; and sealing between the electrode wire and the current supply hole is performed using glue for waterproofing.

15. The electrode structure of claim 13, wherein at least one support protrusion is formed on the head portion of each transducer holder to protrude from a bottom surface of the seating groove, to support a lower surface of the respective transducer and to form a separation space between the transducer and the bottom surface.

16. The electrode structure of claim 13, wherein, in the head portion of each transducer holder, at least a part of the side surface of the seating groove is formed to be open.

17. The electrode structure of claim 13, wherein a locking protrusion is formed on the head portion of each transducer holder to protrude from the bottom surface of the seating groove and to have a tip bent inwardly so as to prevent deviation of the respective transducer inserted into the seating groove.

18. The electrode structure of claim 13, wherein the body portion of each transducer holder comprises:

a shaft portion extending from the head portion backward and being pressed into the coupling hole; and a screw portion extending from the shaft portion backward and coupled to the fastening member in the rear of the ultrasonic radiation frame after passing through the coupling hole;

sealing between the transducer holder and the ultrasonic radiation frame is performed using a sealing member; and the sealing member comprises an O-ring inserted outside the shaft portion, and an O-ring pressing member inserted outside the shaft portion from a rear of the O-ring and allowing the O-ring to be in close contact with the rear surface of the ultrasonic radiation frame.

19. The electrode structure of claim 13, wherein adhesion between at least one of the rear surface and the side surface of each transducer and the respective transducer holder is performed using an adhering member, and sealing between an inside of the transducer holder and the transducer is performed, so that vibration of the transducer is enabled inside the transducer holder; and sealing between the transducer holder and the ultrasonic radiation frame is performed using a sealing member; and the sealing member comprises an O-ring inserted outside the shaft portion, and an O-ring pressing member inserted outside the shaft portion from a rear of the O-ring and allowing the O-ring to be in close contact with the rear surface of the ultrasonic radiation frame.

20. A device comprises: a high-intensity focused ultrasound generation device including the electrode structure of claim 1.

* * * * *